(12) United States Patent
Almo et al.

(10) Patent No.: US 11,279,728 B2
(45) Date of Patent: Mar. 22, 2022

(54) BROAD SPECTRUM VIRAL INHIBITOR

(71) Applicants: Albert Einstein College of Medicine, Bronx, NY (US); The Penn State Research Foundation, University Park, PA (US)

(72) Inventors: Steven C. Almo, Pelham, NY (US); Tyler Grove, Bronx, NY (US); Anthony Gizzi, Baltimore, MD (US); Craig E. Cameron, State College, PA (US); James J. Arnold, State College, PA (US)

(73) Assignees: Albert Einstein College of Medicine, Bronx, NY (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 16/640,845

(22) PCT Filed: Aug. 21, 2018

(86) PCT No.: PCT/US2018/047202
§ 371 (c)(1),
(2) Date: Feb. 21, 2020

(87) PCT Pub. No.: WO2019/040418
PCT Pub. Date: Feb. 28, 2019

(65) Prior Publication Data
US 2020/0361982 A1    Nov. 19, 2020

Related U.S. Application Data

(60) Provisional application No. 62/548,425, filed on Aug. 22, 2017.

(51) Int. Cl.
*C07H 19/10* (2006.01)
*C07H 19/06* (2006.01)
*A61P 31/14* (2006.01)

(52) U.S. Cl.
CPC ............. *C07H 19/10* (2013.01); *A61P 31/14* (2018.01); *C07H 19/06* (2013.01)

(58) Field of Classification Search
None
See application file for complete search history.

(56) References Cited

U.S. PATENT DOCUMENTS

| 8,759,318 B2 | 6/2014 | Chamberlain et al. |
| 2003/0069256 A1 * | 4/2003 | Torrance ................. A61P 43/00 514/256 |

OTHER PUBLICATIONS

Jain et al., Journal of Organic Chemistry, 1974, vol. 39(1), pp. 30-38. (Year: 1974).*
Petrova etal, Organic Letters, 2011, 13(16), pp. 4200-4203. (Year: 2011).*
Tritten et al., "Metabolic Profiling Framework for Discovery of Candidate Diagnostic Markers of Malaria", Scientific Reports, vol. 3, 2013, pp. 1-7.
Hinrichs et al., "Absolute configuration of Rp-uridine 3', 5'-cyclic phosphorothioate", Nucleic Acids Research, vol. 15, No. 12, 1987, pp. 4945-4955.

* cited by examiner

*Primary Examiner* — Traviss C McIntosh, III
(74) *Attorney, Agent, or Firm* — Fox Rothschild LLP

(57) ABSTRACT

Compounds and methods for treating viral infections and reducing viral multiplication, including flaviviruses. Provided is a derivative of a compound or a pharmaceutical salt thereof, wherein the compound comprises a 3',4-didehydroribose.

19 Claims, 6 Drawing Sheets
Specification includes a Sequence Listing.

SEQUENCE LISTING

<160> NUMBER OF SEQ ID NOS: 5

<210> SEQ ID NO 1
<211> LENGTH: 3
<212> TYPE: DNA
<213> ORGANISM: Artificial Sequence
<220> FEATURE:
<223> OTHER INFORMATION: Dengue virus

<400> SEQUENCE: 1 ggc                                                                 3

<210> SEQ ID NO 2
<211> LENGTH: 20
<212> TYPE: DNA
<213> ORGANISM: Artificial Sequence
<220> FEATURE:
<223> OTHER INFORMATION: Dengue Virus

<400> SEQUENCE: 2
ccguuucucc uucucgauuu                                              20

<210> SEQ ID NO 3
<211> LENGTH: 15
<212> TYPE: DNA
<213> ORGANISM: Artificial Sequence
<220> FEATURE:
<223> OTHER INFORMATION: Dengue Virus

<400> SEQUENCE: 3
ggcaaagagg aagag                                                   15

<210> SEQ ID NO 4
<211> LENGTH: 16
<212> TYPE: DNA
<213> ORGANISM: Artificial Sequence
<220> FEATURE:
<223> OTHER INFORMATION: Dengue Virus

<400> SEQUENCE: 4
ggcaaagagg aagagc                                                  16

<210> SEQ ID NO 5
<211> LENGTH: 20
<212> TYPE: DNA
<213> ORGANISM: Artificial Sequence
<220> FEATURE:
<223> OTHER INFORMATION: Dengue Virus

<400> SEQUENCE: 5
ggcaaagagg aagagcuaaa                                              20

BROAD SPECTRUM VIRAL INHIBITOR

CROSS-REFERENCE TO RELATED APPLICATIONS

This application claims benefit of U.S. Provisional Application No. 62/548,425, filed Aug. 22, 2017, the contents of which are hereby incorporated by reference.

STATEMENT OF GOVERNMENT SUPPORT

This invention was made with government support under grant numbers GM118303, AI133329, GM094662, GM093342 and AI045818 awarded by the National Institutes of Health. The government has certain rights in the invention.

Throughout this application various publications are referred to in brackets. Full citations for these references may be found at the end of the specification. The disclosures of these publications, and of all patents, patent application publications and books referred to herein, are hereby incorporated by reference in their entirety into the subject application to more fully describe the art to which the subject invention pertains.

BACKGROUND OF THE INVENTION

New treatments for flaviviral (e.g., Dengue) infections are critical as no vaccine or drug has yet become available against the Dengue virus. Another flavivirus, Zika virus, has become a leading cause of serious illness and death in some Asian and Latin American countries, and is impinging on the United States. Enormous efforts by academic and commercial entities have resulted in the discovery and development of new antiviral agents; nonetheless, viruses continue to be major public health challenges. (1)

Viperin (virus-inhibitory protein, endoplasmic reticulum associated, interferon (IFN) inducible)) is an IFN-inducible protein (2,3) that inhibits and/or is involved in the replication of a remarkable range of viruses, including chikungunya virus (4), Bunyamwera virus, dengue virus (5), Tick-borne encephalitis virus (6), influenza A virus (7), West Nile virus (5), human cytomegalovirus (8), hepatitis C virus (9), sindbis virus (10), Japanese encephalitis virus (10), HIV-1 (11) and other DNA and RNA viruses (3). Viperin has been suggested to interact or co-localize with seven human proteins (mitochondrial antiviral-signaling protein (MAVS)(12) farnesyl pyrophosphate synthase (FPPS)(7), mitochondrial trifunctional protein (HadHB)(3), interleuken-1 receptor-associated kinase 1 (IRAK1)(13), TNF receptor associated factor 6 (TRAF6)(13) and cytosolic iron-sulfur assembly component 1 (CIAO1))(6), and at least three viral proteins (Dengue fever virus Non-structural protein 3 (NS3)(14, 15), Hepatitis-C virus Non-structural protein 5A (NSSA)(14) and Human cytomegalovirus viral mitochondria-localized inhibitor of apoptosis (vMIA))(3). The physiological roles of these putative viperin interacting proteins are highly diverse, including metabolism, signaling, iron-sulfur cluster formation and isoprenoid biosynthesis, and do not support a common shared mechanism for antiviral function. Furthermore, mechanistic details governing these putative interactions remain incomplete, as they are all based on indirect methods (e.g., yeast-two-hybrid and immunoprecipitation), and in no case has direct binding been validated by quantitative biochemical approaches. Given the large number of proposed interactions and the enormous functional diversity of these putative interactions, a unifying mechanism for viperin function is lacking.

Viperin is a member of the radical S-adenosylmethionine (RS) superfamily of enzymes, which includes over 114,000 sequences from all kingdoms of life. (16) RS enzymes carry out myriad enzymatic reactions, including—among many others—sulfur insertion, methylation of $sp^2$ and $sp^3$ carbons, protein maturation, small molecule racemization and oxidation, oxidative decarboxylation, and numerous complex rearrangements. (17,18) All characterized members of the RS superfamily bind a highly oxygen-sensitive [4Fe-4S] cluster (FeS), which is ligated by three cysteine residues most often found in a highly conserved $CX_3CX_2C$ motif. (19-21) In vivo studies have demonstrated the FeS cluster is essential for viperin function, as substitution of any cysteine residue in this conserved motif negatively impacts antiviral activity. (6,22) This behavior strongly suggests that the potent antiviral activity of viperin is linked to its RS chemistry. As with all characterized members of the RS superfamily, SAM binds to the viperin FeS cluster and undergoes reductive homolytic cleavage to generate one equivalent each of 5'deoxyadenosine radical (5'-dA•) and methionine (18,21,23). Typically, the 5'dA• initiates chemistry by abstracting a hydrogen atom from the cognate substrate, with the ensuing substrate-resident radical species enabling a wide range of transformations. Mammalian viperins are 42kDa proteins composed of three distinct domains: 1) an N-terminal amphipathic α-helix that directs localization to the endoplasmic reticulum (ER)(24); 2) a highly conserved central radical SAM domain; and 3) a C-terminal region reported to be essential for protein-protein interactions, and loading of FeS clusters (23). While the amphipathic N-terminal domain of viperin has been shown to be important for ER-localization, variants of viperin lacking this domain still support antiviral activity, albeit at attenuated levels (6,12, 15,23).

The present invention addresses the need for new treatments for treating flavivirus infections and also, more broadly, inhibiting viral RNA-dependent RNA-polymerases.

SUMMARY OF THE INVENTION

Provided is a derivative of a compound or a pharmaceutical salt thereof, wherein the compound comprises a 3',4'-didehydroribose. The derivative of the compound or a pharmaceutical salt thereof is non-naturally occurring. In an embodiment of the compound is 3'-deoxy-3',4'-didehydro cytidine triphosphate. The derivative or pharmaceutical salt thereof comprises a 3',4'-didehydro structure. As such, it can act as a chain terminator in nucleic acid synthesis.

Provided is a non-naturally occurring derivative of a 3',4'-didehydro compound or pharmaceutical salt thereof, wherein the 3',4'-didehydro compound has the following formula and is derivatized at one or more of the phosphate group positions:

A pharmaceutical composition is provided comprising the derivative of a compound or pharmaceutical salt thereof of as described herein. In an embodiment, the pharmaceutical composition comprises a pharmaceutically acceptable carrier.

A method is provided of treating a flavivirus infection in a subject comprising administering to the subject an amount of the derivative of the compound or pharmaceutical salt thereof, or pharmaceutical composition, as described herein effective to treat a flavivirus infection.

A method is provided of treating a viral infection in a subject comprising administering to the subject an amount of the derivative of the compound or pharmaceutical salt thereof, or pharmaceutical composition, as described herein effective to treat a viral infection.

A method is provided of inhibiting a viral RNA-dependent RNA-polymerase comprising contacting the viral RNA-dependent RNA-polymerase in a cell with an amount of the derivative of the compound or pharmaceutical salt thereof, or pharmaceutical composition, as described herein, effective to inhibit a viral RNA-dependent RNA-polymerase.

A method is provided of inhibiting multiplication of a virus, which virus uses a viral RNA-dependent RNA-polymerase, comprising contacting the virus with an amount of the derivative of the compound or pharmaceutical salt thereof, or pharmaceutical composition, as described herein, effective to inhibit viral multiplication. In an embodiment, the viral RNA-dependent RNA-polymerase is a supergroup II RNA-dependent RNA-polymerase. In an embodiment, the viral RNA-dependent RNA-polymerase is not a supergroup I RNA-dependent RNA-polymerase.

Additional objects of the invention will be apparent from the description which follows.

DETAILED DESCRIPTION OF THE INVENTION

Figures 1A, 1B, 1C, 1D, 1E, 1F:
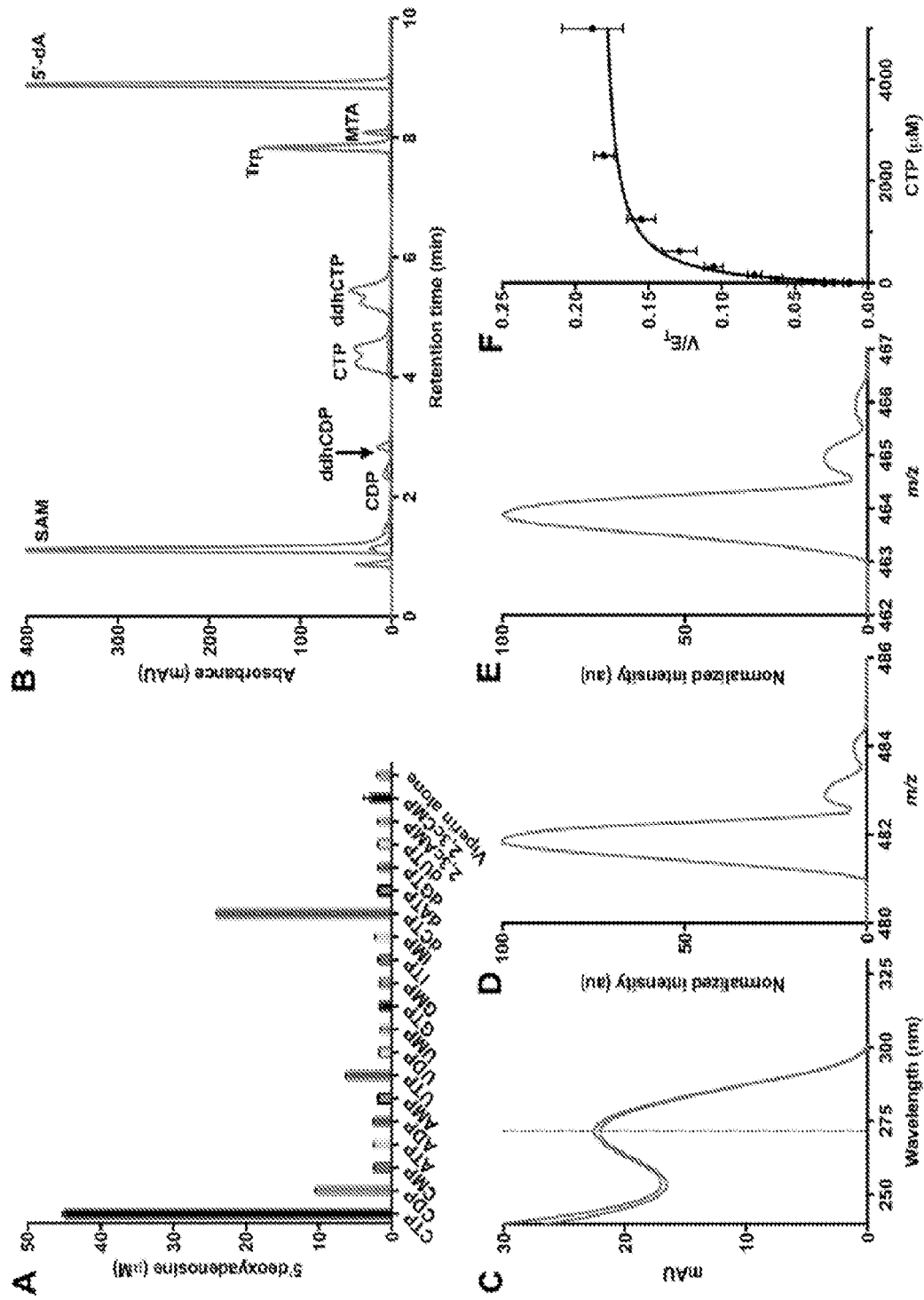
FIG. 1(A)-1(F): Substrate specificity of viperin (A) a panel of nucleotides and deoxynucleotides were mixed individually with rVIP and incubated at 37° C. for four minutes and the resulting 5'-deoxyadenosine production was measured. Error bars represent the mean±SD of three replicates. (B) HPLC analysis showing conversion of CTP to new product (time=0 minutes, blue trace; and time=45 minutes, red trace). The presence of the viperin-dependent diphosphate species (ddhCDP) is a nonenzymatic breakdown product of ddhCTP, the product of the viperin reaction; it is not appreciably formed when CDP is used as a substrate. (C) UV-visible spectrum of CTP (blue trace) and ddhCTP (red trace). The dotted line shows the absorbance maximum to be at 271 nm. (D). Mass to charge ratio of CTP (blue, m/z=482.1) and (E) ddhCTP (red, m/z=251). (F) Kinetic analysis of rVIP with CTP. rVIP Km for CTP=182.8±27.6 μM and Vmax=0.185±0.007 minutes-1. Error bars represent the mean±SD of three replicates.

Viral infections of all kinds continue to represent major public health challenges, demanding enhanced mechanistic understanding of the processes contributing to viral life-cycles for the realization of new therapeutic strategies. Viperin, a member of the radical S-adenosyl-L-methionine (SAM) superfamily of enzymes, is an interferon inducible protein that inhibits the replication of a remarkable range of RNA and DNA viruses, including influenza A virus, West Nile virus, rhinovirus, hepatitis C virus, and HIV. Viperin itself has been suggested to elicit these broad antiviral activities through interaction with a large number of functionally unrelated host and viral proteins. In contrast, herein it is demonstrated that viperin converts cytidine triphosphate (CTP) to 3'-deoxy-3',4'-didehydro-CTP (ddhCTP), a previously undescribed biologically relevant molecule, via a SAM-dependent radical mechanism. It is demonstrated that mammalian cells expressing viperin, and macrophages stimulated with IFN-α, produce substantial quantities of ddhCTP. Also disclosed herein is that ddhCTP acts as a chain terminator for the RNA-dependent RNA-polymerase from Dengue virus (DV). These findings provide a unifying mechanism, based on intrinsic catalytic/enzymatic properties, for the broad viral effects of viperin, which involves the generation of a replication chain terminator encoded by mammalian genomes.

A derivative of a compound or pharmaceutical salt thereof, wherein the compound comprises a 3',4'-didehydroribose.

In an embodiment of the derivative of the compound or pharmaceutical salt thereof, the compound has the following formula:

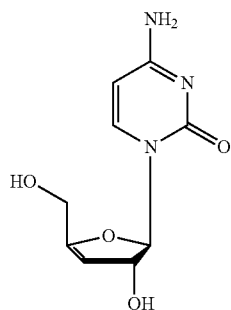 [SMILES: Nc1ccn([C@@H]2OC(CO)=C[C@@H]2O)c(=O)n1]

or is 3'-deoxy-3',4'-didehydro cytidine triphosphate.

In an embodiment of the derivative of the compound or pharmaceutical salt thereof, the derivative comprises the following formula:

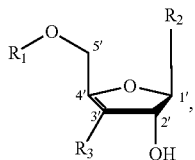

(Formula I)

wherein, in Formula I, $R_1$ is a hydrogen, alkyl, benzyl, aryl, acycloxyalkyl, alkoxycarbonyloxy alkyl, or S-acylthioalkyl; and $R_2$ is an adenine, guanosine, cytosine, uridine, thymidine, or a derivative of adenine, guanosine, cytosine, uridine, or thymidine; and $R_3$ is a hydrogen, hydroxyl, thiol, halide, or alkyl.

In an embodiment of the derivative of the compound or pharmaceutical salt thereof, the derivative comprises the following formula:

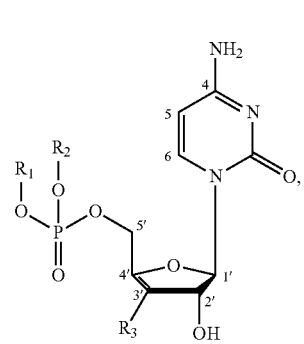

(Formula II)

wherein, in Formula II, $R_1$ and $R_2$ are each, independently, a hydrogen, alkyl, benzyl, aryl, acycloxyalkyl, alkoxycarbonyloxy alkyl, or S-acylthioalkyl; and $R_3$ is a hydrogen, hydroxyl, thiol, halide, or alkyl.

In an embodiment of the derivative of the compound or pharmaceutical salt thereof, the derivative comprises the following formula:

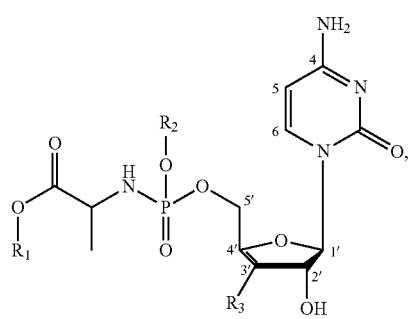

(Formula III)

wherein, in Formula III, $R_1$ and $R_2$ are each, independently, a hydrogen, alkyl, benzyl, aryl, acycloxyalkyl, alkoxycarbonyloxy alkyl, or S-acylthioalkyl; and $R_3$ is hydrogen, hydroxyl, thiol, halide, or alkyl.

In an embodiment of the derivative of the compound or pharmaceutical salt thereof, the derivative comprises the following formula:

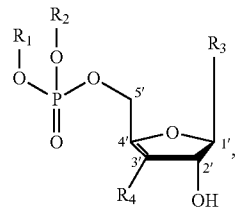

(Formula IV)

wherein, in Formula IV, $R_1$ and $R_2$ are each, independently, a hydrogen, alkyl, benzyl, aryl, acycloxyalkyl, alkoxycarbonyloxy alkyl, or S-acylthioalkyl;

$R_3$ is adenine, guanosine, cytosine, uridine, thymidine, or a derivative of adenine, guanosine, cytosine, uridine, or thymidine; and $R_4$ is hydrogen, hydroxyl, thiol, halide, or alkyl.

In an embodiment of the derivative of the compound or pharmaceutical salt thereof, the derivative comprises the following formula:

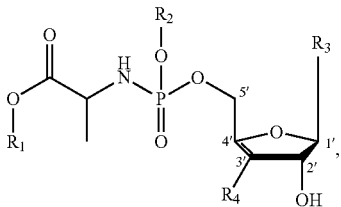

(Formula V)

wherein, in Formula V, $R_1$ and $R_2$ are each, independently, a hydrogen, alkyl, benzyl, aryl, acycloxyalkyl, alkoxycarbonyloxy alkyl, or S-acylthioalkyl;

$R_3$ is adenine, guanosine, cytosine, uridine, thymidine, or a derivative of adenine, guanosine, cytosine, uridine, or thymidine; and $R_4$ is hydrogen, hydroxyl, thiol, halide, or alkyl.

In an embodiment of the derivative of the compound or pharmaceutical salt thereof, the derivative comprises the following formula:

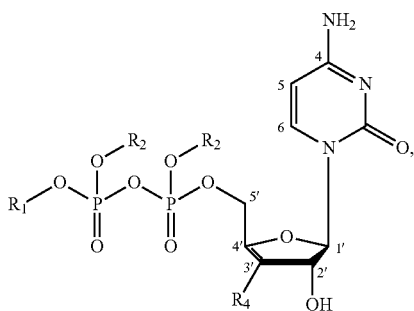

(Formula VI)

wherein, in Formula VI, $R_1$, $R_2$, and $R_3$ are each, independently, a hydrogen, alkyl, benzyl, aryl, acycloxyalkyl, alkoxycarbonyloxy alkyl, or S-acylthioalkyl; and $R_4$ is hydrogen, hydroxyl, thiol, halide, or alkyl.

In an embodiment of the derivative of the compound or pharmaceutical salt thereof, the derivative comprises the following formula:

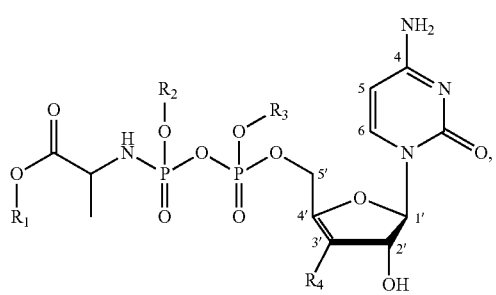

(Formula VII)

wherein, in Formula VII, $R_1$, $R_2$, and $R_3$ are each, independently, a hydrogen, alkyl, benzyl, aryl, acycloxyalkyl, alkoxycarbonyloxy alkyl, or S-acylthioalkyl; and $R_4$=hydrogen, hydroxyl, thiol, halide, or alkyl.

In an embodiment of the derivative of the compound or pharmaceutical salt thereof, the derivative comprises the following formula:

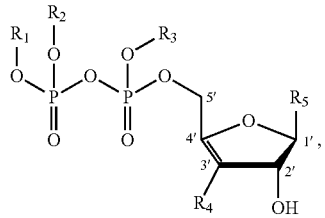

(Formula VIII)

wherein, in Formula VIII, $R_1$, $R_2$, and $R_3$ are each, independently, a hydrogen, alkyl, benzyl, aryl, acycloxyalkyl, alkoxycarbonyloxy alkyl, or S-acylthioalkyl;

$R_5$ is adenine, guanosine, cytosine, uridine, thymidine, or a derivative of adenine, guanosine, cytosine, uridine, or thymidine; and $R_4$ is hydrogen, hydroxyl, thiol, halide, or alkyl.

In an embodiment of the derivative of the compound or pharmaceutical salt thereof, the derivative comprises the following formula:

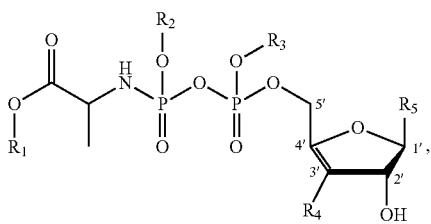

(Formula IX)

wherein, in Formula IX, $R_1$, $R_2$, and $R_3$ are each, independently, a hydrogen, alkyl, benzyl, aryl, acycloxyalkyl, alkoxycarbonyloxy alkyl, or S-acylthioalkyl;

$R_5$ is adenine, guanosine, cytosine, uridine, thymidine, or a derivative of adenine, guanosine, cytosine, uridine, or thymidine; and $R_4$ is hydrogen, hydroxyl, thiol, halide, or alkyl.

A non-naturally occurring derivative of a didehydro compound or pharmaceutical salt thereof, wherein the didehydro compound has the following formula and is derivatized at one or more of the phosphate group positions:

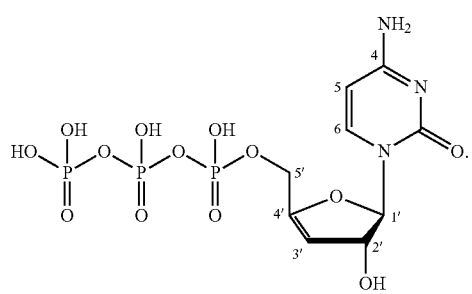 [SMILES: Nc1ccn([C@@H]2OC(COP(=O)(O)OP(=O)(O)OP(=O)(O)O)=C[C@@H]2O)c(=O)n1]

In an embodiment, the alkyl, benzyl, aryl, acycloxyalkyl, alkoxycarbonyloxy alkyl, or S-acylthioalkyl as recited herein is unsubstituted. In an embodiment, the alkyl, benzyl, aryl, acycloxyalkyl, alkoxycarbonyloxy alkyl, or S-acylthioalkyl as recited herein is substituted. In an embodiment, the substitution is an alkyl, benzyl, aryl, acycloxyalkyl, alkoxycarbonyloxy alkyl, or S-acylthioalkyl. In an embodiment, the substitution is a heteroaryl or heterocycle.

As used herein, "alkyl" includes both branched and straight-chain saturated aliphatic hydrocarbon groups having the specified number of carbon atoms and may be unsubstituted or substituted. Thus, C1-C5 as in "C1-C5 alkyl" is defined to include groups having 1, 2, 3, 4 or 5 carbons in a linear or branched arrangement and specifically includes methyl, ethyl, n-propyl, isopropyl, n-butyl, t-butyl, and pentyl.

As used herein "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

The term "heterocycle" as used herein refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1, 3-oxathiolane, and the like.

The term "heteroaryl" as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom. selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyriinidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

In the compounds of the present invention, in an embodiment where the functional groups are substituted, they can be further substituted by replacing one or more hydrogen atoms be alternative non-hydrogen groups. These include, but are not limited to, halo, hydroxy, mercapto, amino, carboxy, cyano and carbamoyl.

The term "substituted" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon (s) or hydrogen (s) atom are replaced by one or more bonds, including double or triple bonds, to a heteroatom. Examples of substituent groups include the functional groups described above, and, in particular, halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity. Moreover, where hydrogens are not shown in the carbon-based structures herein, implicit hydrogens are understood to complete valences as required. All carbon valencies not otherwise engaged are saturated with hydrogen as per convention. Thus, —H is not generally shown in the carbon-based structures, but "—H" can be specified as one embodiment of a given R group.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The term "pharmaceutical salt" as used herein refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

As used herein, a "pharmaceutical composition" is not in of itself naturally occurring.

A pharmaceutical composition is provided comprising the derivative of a compound or pharmaceutical salt thereof of as described herein. In an embodiment, the pharmaceutical composition comprises a pharmaceutically acceptable carrier.

A method is provided of treating a flavivirus infection in a subject comprising administering to the subject an amount of the derivative of the compound or pharmaceutical salt thereof, or pharmaceutical composition, as described herein effective to treat a flavivirus infection.

In an embodiment, the flavivirus infection is a Dengue virus infection, Zika virus infection, or West Nile virus infection.

A method is provided of treating a viral infection in a subject comprising administering to the subject an amount of the derivative of the compound or pharmaceutical salt thereof, or pharmaceutical composition, as described herein effective to treat a viral infection.

In an embodiment, the viral infection is an influenza virus infection or a hepatitis C virus infection or an HIV infection. In an embodiment, the viral infection is not a picornavirus infection. In an embodiment, the viral infection is not a rhinovirus infection.

In an embodiment, administration can be auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, uretheral, or vaginal.

A method is provided of inhibiting a viral RNA-dependent RNA-polymerase comprising contacting the viral RNA-dependent RNA-polymerase in a cell with an amount of the derivative of the compound or pharmaceutical salt thereof, or pharmaceutical composition, as described herein, effective to inhibit a viral RNA-dependent RNA-polymerase.

A method is provided of inhibiting multiplication of a virus, which virus uses or expresses a viral RNA-dependent RNA-polymerase, comprising contacting the virus with an amount of the derivative of the compound or pharmaceutical salt thereof, or pharmaceutical composition, as described herein, effective to inhibit viral multiplication. In an embodiment, the viral RNA-dependent RNA-polymerase is a supergroup II RNA-dependent RNA-polymerase. In an embodiment, the viral RNA-dependent RNA-polymerase is not a supergroup I RNA-dependent RNA-polymerase.

This invention will be better understood from the Experimental Results, which follow. However, one skilled in the art will readily appreciate that the specific methods and results discussed are merely illustrative of the invention as described more fully in the claims that follow thereafter.

Experimental Results

In vitro characterization of Viperin activity: Previous reports indicated that removal of the N-terminal amphipathic domain was necessary to generate stable and soluble recombinant viperin protein. (25,26) Therefore, we used a truncated construct of *Rattus norvegicus* (residues 51-361) viperin (Rvip) to perform in vitro assays, because it yielded ~100 mg of purified protein per L of fermentation, and was readily soluble to concentrations >2 mM. A recent study demonstrated that purified viperin was not capable of modifying, interacting with, or inhibiting FPPS. (27) This report was confirmed and these studies expanded to include two additional putative interacting proteins. Under the conditions tested, direct interaction between viperin and purified FPPS, NS5A or HadHB could not be detected. Therefore, to gain insight, genome context analysis was used, as it is well documented that protein fusions can allow for the function of fused gene products to be inferred when one of the partners has a predicted/annotated function. (28) A search of distant homologues of viperin yielded one such fusion; the viperin homologue from *Lacinutrix mariniflava* is fused at the N-terminus with a predicted cytidylate monophosphate kinase. Next, eukaryotic genomes were examined and in every instance found that viperin was immediately adjacent to a gene annotated as cytidylate monophosphate kinase 2 (CMPK2). Indeed, the viperin-CMPK2 linkage is conserved throughout chordate evolution as noted by Lei, et. al. (29)

To investigate whether viperin modifies a nucleotide, viperin was screened against a diverse set of nucleotides and deoxynucleotides, and enhanced 5'dA formation—an indicator of substrate activation—was looked for. In a typical screening assay 50 μM Rvip was mixed with 2 mM SAM, and 1 mM nucleotide/deoxynucleotide and 5 mM dithionite (a low-potential artificial reductant), and the reaction was allowed to proceed for 4 min. Rvip, like most other RS proteins, performs reductive cleavage of SAM in the absence of substrates. However, as shown in FIG. 1A, CTP activates 5'dA production by Rvip by 30-fold relative to protein alone. Next, the products from a reaction of CTP and Rvip were separated by liquid chromatography (LC), and the formation of two new peaks was seen: one for 5'dA (retention time of 9.1 min) and one for an unknown product with a retention time of 5.2 min (FIG. 1B). This new product had a UV-visible spectrum similar to CTP, indicating that the pyrimidine ring is not drastically modified during the reaction (FIG. 1C). Using LC-coupled mass spectrometry (LC-MS) in negative mode, the new compound exhibited a negative ion mass to charge ratio (m/z) of 464.1, which is 18 Da less than the m/z 482.1 of CTP (FIGS. 1D and 1E).

Figure 3:
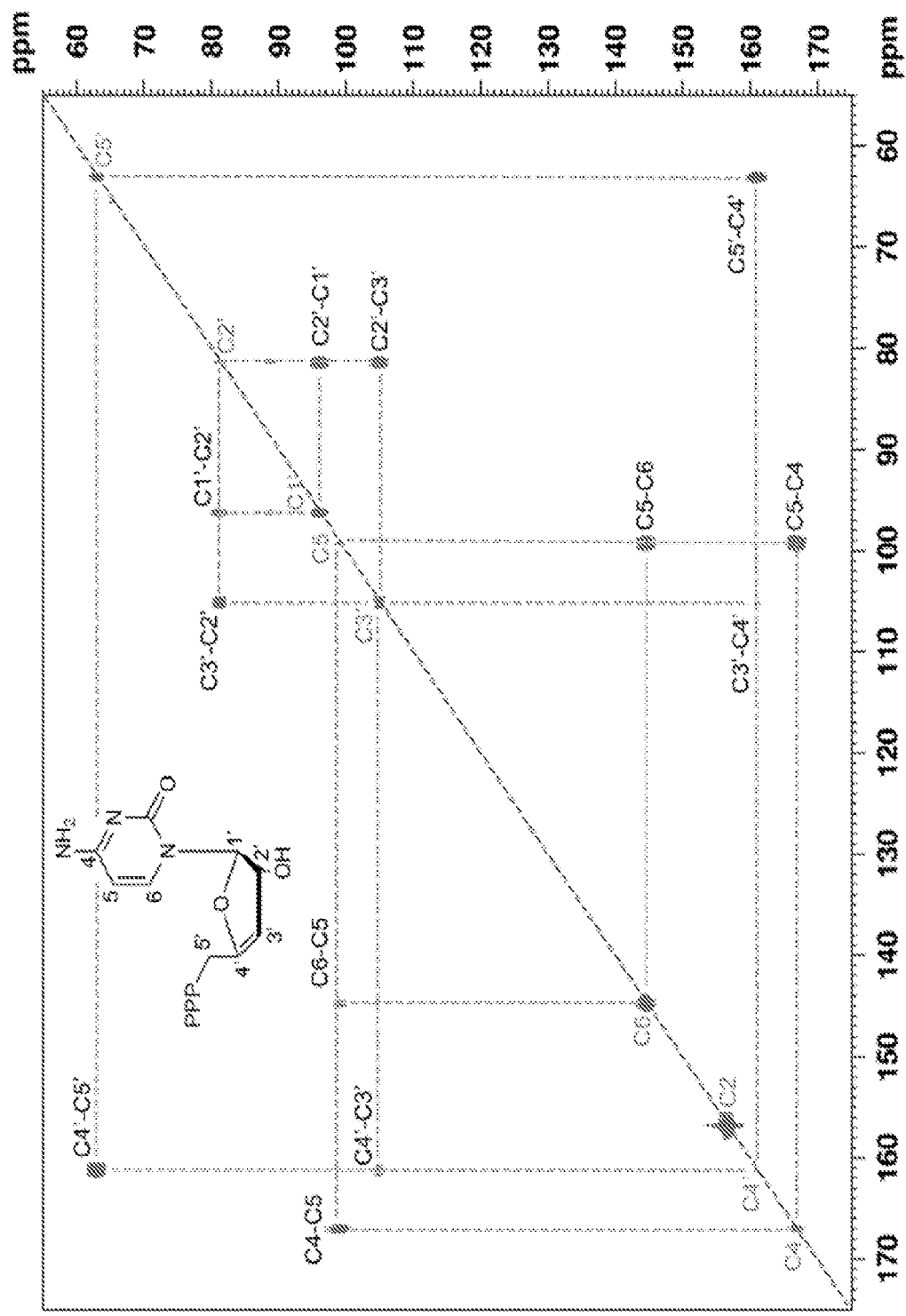
FIG. 3: $^{13}$C-$^{13}$C COSY spectrum of $^{13}$C9$^{15}$N3-ddhCTP. The assignments for the observed correlations of the $^{13}$C-connectivities are indicated with the grey dotted lines.

Uniformly labeled or natural abundance (n.a.) viperin product was produced by reacting Rvip with SAM and either 1 mM CTP or $^{13}C_9$, $^{15}N_3$-CTP in a 3 mL reaction. The viperin product was purified by anion exchange chromatography. The structure of the CTP-derived viperin-catalyzed product was determined by solution NMR techniques. $^{13}C$-$^{13}C$ COSY NMR on the uniformly labeled viperin product unambiguously defined its carbon-carbon connectivity, which demonstrated that the carbon backbone was unchanged from the CTP starting material (FIG. 3). Comparison of the $^1H$-$^{13}C$ $^2D$ HSQC chemical shift data of the n.a. viperin product with those of CTP, indicated several shifts between the two compounds, with the most notable being of the complete loss of the 4' proton signal at 4.27 ppm. In addition, analysis of the $^{13}C$-$^{13}C$ COSY indicates that the C4' carbon resonance had shifted from 85.4 ppm to 161.2 during the conversion of CTP to the new product. Comparison of the $^1H$-$^{13}C$ $^2D$-HSQC NMR spectra derived from synthetic 3'-deoxy-3',4'-didehydro-cytidine (30) and n.a. viperin product exhibited nearly complete overlap, with the exception of the 5' position on the ribose, which we attribute to the presence of the triphosphate moiety. Indeed, the $^{31}P$ NMR spectrum of the viperin product exhibited three resonances—at −19.5 (triplet), −9.5 (doublet) and −3.9 (doublet) ppm—which were almost identical to the spectrum of a CTP standard and are consistent with a linear triphosphate functionality. The interpretation of the NMR spectra, along with the above MS data, is consistent with the viperin product being 3'-deoxy-3',4'-didehydro-cytidine triphosphate (ddhCTP), where the loss of the 4'-hydrogen and the 3' hydroxyl group occurs without rearrangement of the carbon skeleton.

Rvip has a $K_m$ of 183±28 µM for CTP and produces ddhCTP with a maximum velocity of 0.185±0.007 min-1 (FIG. 1F). The rate of ddhCTP formation is consistent with that of other RS enzymes with their native substrates (31, 32). The intracellular concentration of CTP is highly dependent on the cell type; however, it typically falls in the 1 mM range, which agrees well with the Km obtained for Rvip for CTP (33). In addition, Rvip produces one molecule of 5'-dA for every molecule of ddhCTP, indicating that the formation of 5'-dA is tightly coupled to the production of ddhCTP. Importantly, Rvip also produces ddhCTP when the reaction is catalyzed by an electron derived from the non-native enzymatic reducing system involving flavodoxin/flavodoxin reductase/NADPH. This behavior eliminates the possibility that dithionite is causing an unanticipated side reaction between Rvip and CTP.

Mechanism of ddhCTP production by viperin: To determine the mechanism of the viperin-catalyzed transformation of CTP to ddhCTP, deuterium tracer experiments were utilized with selectively labeled isotopologues of CTP. When Rvip was incubated with SAM and CTP deuterated at the 2', 3', 4', 5' and 5 positions (deuCTP), the negative ion m/z of 5-dA increased from 250.1 to 251.1, consistent with the transfer of one deuterium from deuCTP to 5'-dA•. When ddhCTP from the reaction was analyzed by MS, the product exhibited a negative ion m/z of 468.1, indicating that the deuterium abstracted by 5'-dA during catalysis did not return to the product. To demonstrate that deoxyCTP is not a true substrate, Rvip was coincubated in the presence of 1 mM deuCTP and 1 mM deoxyCTP. 5'-dA produced during this reaction has an m/z of 251.1, which is only consistent with Rvip abstracting a deuteron from deuCTP and not acting on the deoxyCTP (i.e., lack of m/z 250.0). Because deoxynucleotides are typically present at concentrations that are orders of magnitude lower (~40 µM) than their ribonucleotide counterparts (34), and because of the absence of measureable 5'-dA derived from deoxyCTP in the above reaction, we conclude that deoxyCTP is not a substrate for Rvip.

Figures 2A, 2B, 2C, 2D, 2E:
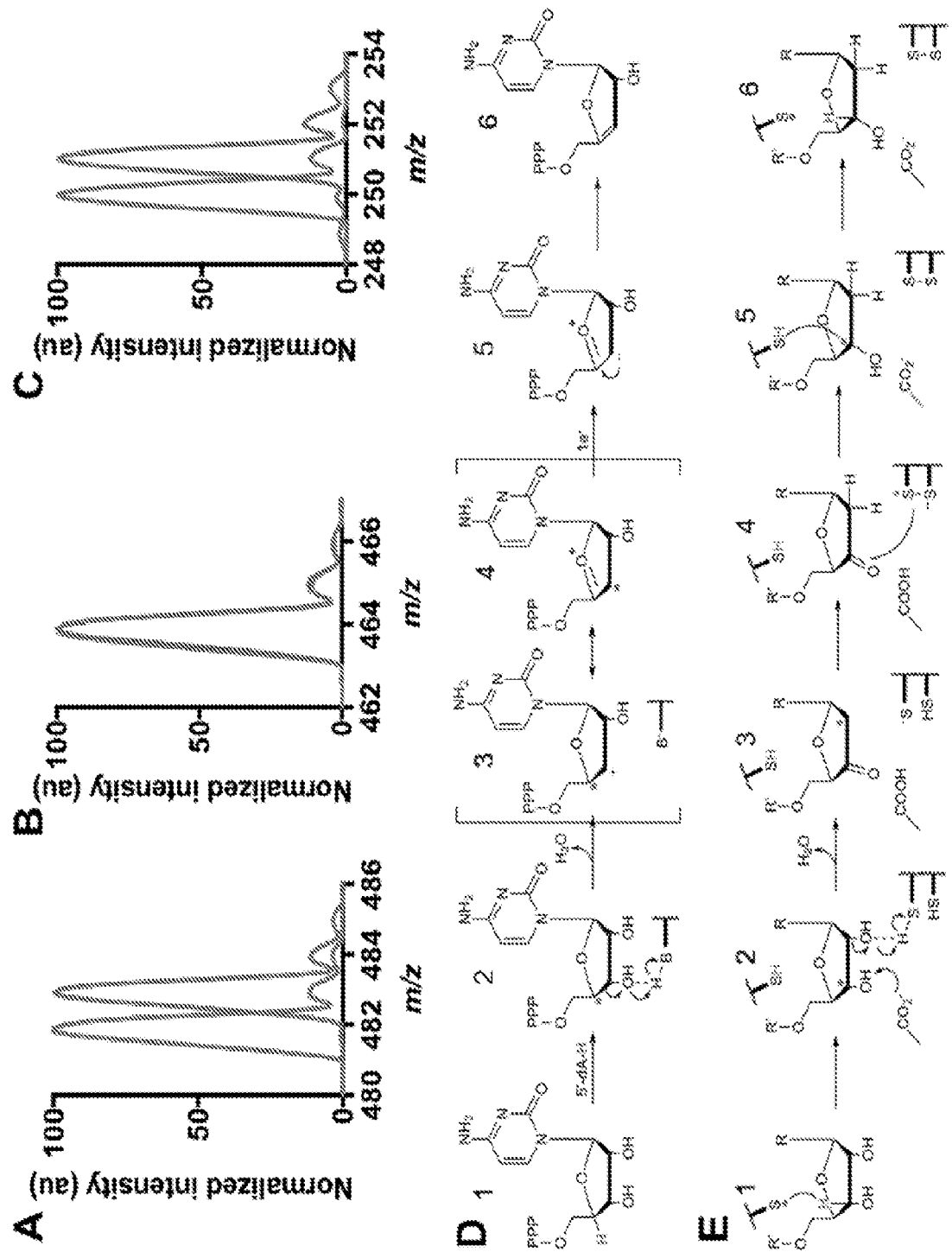
FIG. 2(A)-2(E): Proposed mechanistic model for CTP reduction and formation of ddhCTP by viperin. (A) Mass spectra trace of CTP (left panel, blue trace) or CTP-4'-2H (left panel, red trace) was allowed to react with Rvip for four minutes, and the resulting products (B) were monitored by negative mode ESI and found to contain no deuterium. (C) The resulting 5'-dA from CTP-4'-2H (red trace) increases by one mass unit (m/z=251.1 vs natural abundance m/z=250.1) due to the incorporation of deuterium. The y-axis of each spectrum was normalized to 100% with arbitrary units (au) to allow direct comparison between each sample. (D) Proposed viperin mechanism. Following hydrogen atom abstraction at the 4' position of CTP, general base-assisted loss of the 3' hydroxyl group leads to a carbocation/radical intermediate that is reduced by 1e—to yield the ddhCTP product. (E) Nucleotide reduction mechanism by the *E. coli* class Ia ribonucleotide reductase.

Site specific deuterium-labeled CTP derivatives were generated to determine the position from which 5'-dA• abstracts hydrogen to initiate catalysis. When 4'-2H-CTP (FIG. 2A, m/z 483.1) was incubated with Rvip and SAM, the 5'-dA increases by one mass unit (m/z 251.1, FIG. 2B), while the ddhCTP product shows no increase in m/z over its natural isotopic abundance (FIG. 2C). All other isotopologues of CTP showed no loss of deuterium content in their respective products, as well as no deuterium transfer to 5'-dA. These results are consistent with 5'-dA• initiating chemistry by abstracting hydrogen from the 4' position of CTP (FIG. 2A). A provisional mechanism for the viperin-catalyzed reaction that is consistent with the observations is outlined in FIG. 2D. In this mechanism, Rvip abstracts a hydrogen atom from the 4'-position of the ribose of CTP, which allows for loss of the 3'-hydroxyl group with general acid assistance. The resulting radical cation, which is resonance stabilized, is then reduced by one electron to yield the designated product. This mechanism has precedent in previous studies of ribonucleotide reductase (RNR). (35) Reduction of nucleotides by RNR proceeds through a transient 3'-radical, which is generated by hydrogen atom abstraction by a catalytic active site cysteine radical. Subsequent elimination of the 2'-hydroxyl as water, upon its protonation by an active site residue, generates a keto-radical (FIG. 2E, 3). The keto-radical then oxidizes a pair of active site cysteine residues, producing the antepenultimate 2'-dexoy-3'-ketyl intermediate and a disulfide radical anion (3 to 4). The disulfide radical anion species reduces the 3'-ketyl intermediate by a proton-coupled electron transfer to produce a disulfide and a 3'-radical (FIG. 2E, 4 to 5). This species is quenched by transfer of a hydrogen atom from the active-site cysteine to generate the starting protein cysteine radical and the reduced nucleotide (FIG. 2E, 6). The source of the electron that reduces intermediate 3 (or 4) in the viperin-catalyzed reaction is currently unclear; however, ketyl radicals (e.g. intermediate 3 in the RNR reaction or intermediate 4 in the proposed viperin reaction) are potent oxidants with potentials in the range of +2 V, making this step thermodynamically favorable. (36) We propose that, similar to other RS enzyme reactions (32,37,38), the electron ultimately derives from a reduced FeS cluster, suggesting that viperin would require two electrons to complete each turnover: one to generate the 5'-dA• and another to reduce intermediate 3.

In vitro characterization of CMPK2: Because CMPK2 is always immediately adjacent to viperin in eukaryotic genomes, and is cotranscribed with viperin during cellular stimulation with IFN, (39) human CMPK2 was cloned and purified for in vitro characterization. CMPK2 was reported to catalyze the phosphorylation of CMP, UMP, and dCMP to their corresponding diphosphate products with ATP as the phosphoryl donor (40). However, we find that CMPK2 exhibits significant preference for CDP and UDP as substrates, yielding CTP and UTP, respectively, as products.

The synteny and coordinated expression observed between CMPK2 and viperin may have arisen to ensure sufficient substrate (i.e., CTP) for viperin-mediated catalysis during viral infection.

Figures 4A, 4B:
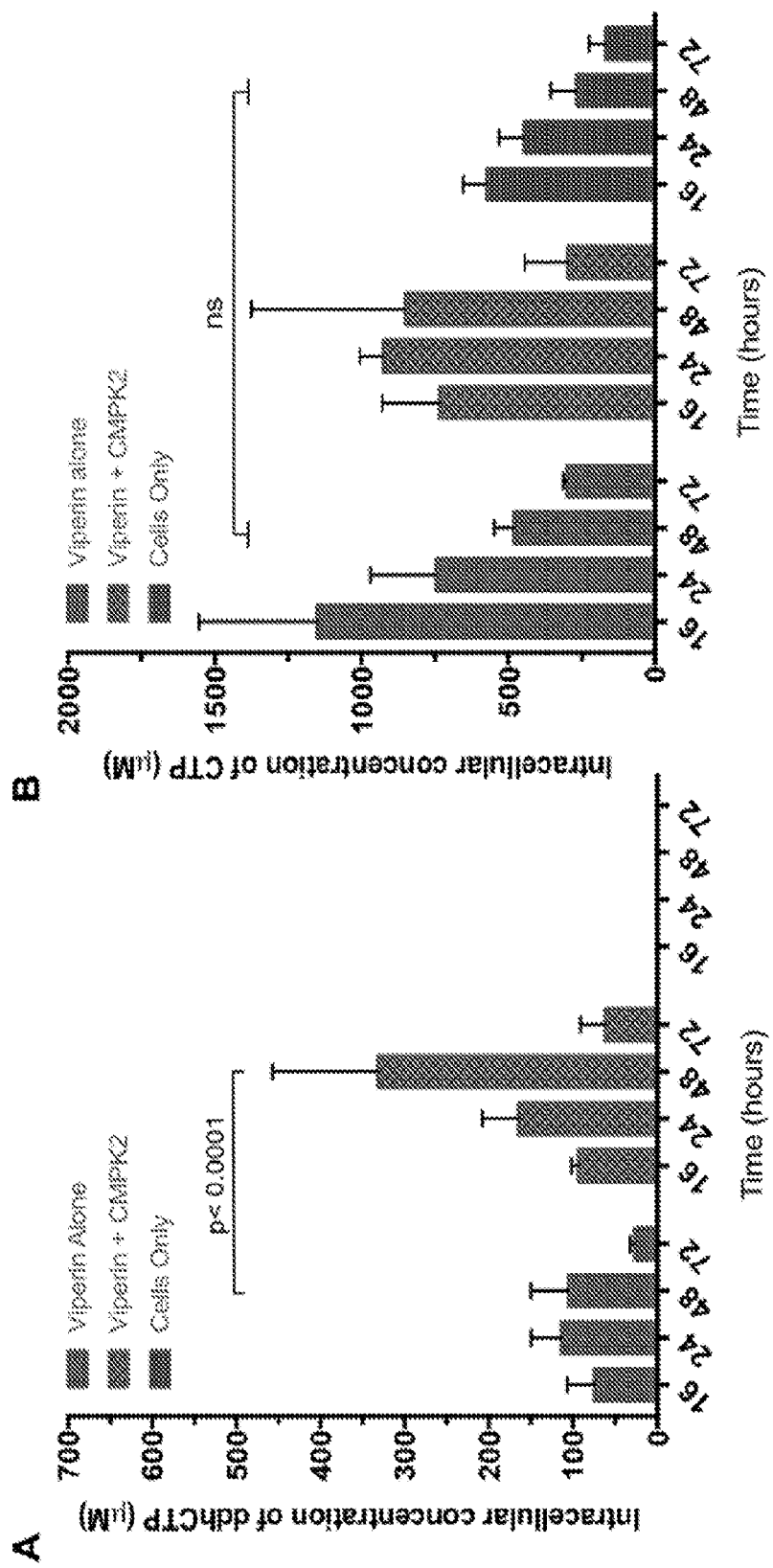
FIG. 4(A)-4(B): Intracellular concentrations of 3'-deoxy-3'4'-didehydro-CTP in HEK293T expressing FLAG-Hs viperin (aqua), FLAG-viperin and Hs CMPK2 (maroon), or empty vector (dark blue). Analysis of ddhCTP formation indicates that the viperin+CMPK2 cells show a statistically significant increase of ~230 μM ddhCTP formation over viperin alone at 48 h post transfection. Statistical significance was determined using a two-way ANOVA with a Tukey post-hoc analysis. Samples were taken at 16 h, 24 h, 48 h, and 72 h, post infection. In the cells only samples there were undetectable levels of 3'-deoxy-3'4'-didehydro-CTP. (B) Intracellular concentrations of CTP did not differ significantly (ns) over time.

Intercellular production of ddhCTP by viperin: To determine whether ddhCTP can be produced in a mammalian cellular environment, we generated a series of human (Hs) viperin and Hs CMPK2 expression constructs for transient transfection in HEK293T cells. It has been reported that HEK293T cells do not express viperin in the presence or absence of IFN 4; therefore, production of ddhCTP would not be expected in the absence of a viperin producing plasmid. HEK293T cells were transfected with a control plasmid, viperin alone, CMPK2 alone, or both viperin and CMPK2. The cells were grown for designated times before cell counting and harvesting. Cell pellets were extracted with a solvent composed of acetonitrile/methanol/water, which contained internal standards at known concentrations and analyzed by LC/MS. In all cases, regardless of the identity of the transfected plasmid(s), it was find that over a 72-hour time course the overall nucleotide pool consistently decreases, most likely due to limiting nutrient levels. In addition, at each time-point there are no statistically significant differences in total nucleotide concentrations between the control, Hs viperin, and Hs viperin/Hs CMPK2 treated cells. Most importantly, HEK293T cells transfected with a control plasmid exhibited ddhCTP levels below our limit of detection (FIG. 4A, right), while HEK293T cells transfected with the Hs viperin plasmid exhibited considerable intracellular ddhCTP levels: ~75 µM after 16-h post transfection (FIG. 4A, left), which decreases to ~35 µM after 72 h. Interestingly, cotransfection of viperin and CMPK2 plasmids resulted in a ~4-fold increase in the amount of ddhCTP to ~330 µM at 48 h (FIG. 4A, middle, maroon, p<0.0001). Moreover, when viperin and CMPK2 are expressed together, the relative intracellular concentrations of ddhCTP to CTP increases over time, while overexpression of viperin alone results in a ratio of ddhCTP to CTP that is essentially unchanged over time. This behavior may allow viperin to continue generating ddhCTP even though ~40% of the total cellular pool of cytidine triphosphates is present as ddhCTP at 48 h. This observation not only demonstrates that viperin is essential for production of ddhCTP, but also suggests that expression of CMPK2 ensures that CTP, in the presence of viperin, is not limiting.

Figures 5A, 5B:
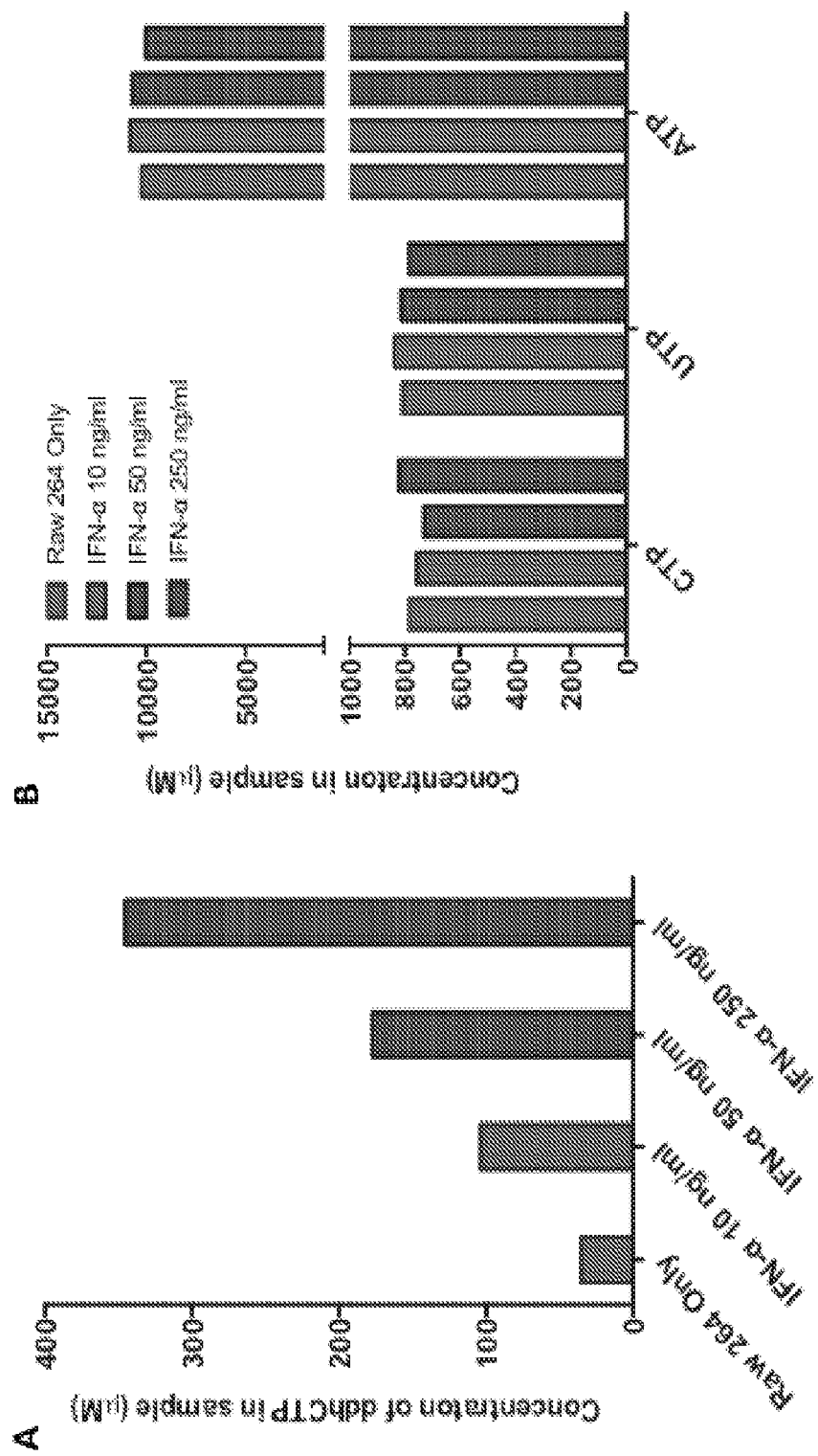
FIG. 5: Intracellular concentration of ddhCTP, CTP, UTP and ATP in immortalized macrophage cells (RAW 264.7) grown in serum free media in the presence of increasing concentrations of murine IFN-alpha (10 ng/mL, 50 ng/mL and 250 ng/mL).

Viperin has been shown to be expressed in most human cell types at very low levels; however, viperin expression can be robustly induced in immune cells, such as macrophages and neutrophils, by interferon, lipopolysaccharide and double-stranded RNA analogues (e.g., polyinosinic-polycytidylic acid)(41,42). Therefore, immortalized murine macrophages (RAW264.7) were cultured in the absence or presence of IFN-α in serum free media, as it has been previously shown that RAW264.7 produce increasing amounts of viperin in an IFN-α-sensitive fashion. (43) When these RAW264.7 cells were harvested after 19 h and analyzed by LC-MS, the concentration ddhCTP was shown to be highly dependent on the concentration of IFN-α (FIG. 5A). RAW264.7 cells cultured in the presence of 250 ng/mL of IFN-α generated intracellular concentrations of ddhCTP that reach nearly 350 µM (FIG. 5A). Intracellular concentrations of ATP, UTP and CTP were also measured. Remarkably, even at the highest concentrations of IFN-α, the intracellular concentrations of these nucleoside triphosphates remain unperturbed (FIG. 5B). Analogous to the behavior it was observed that HEK293T cells cotransfected with viperin and CMPK2, with 250 ng/mL of IFN-α the relative concentrations of ddhCTP (~350 µM) to CTP (~800 µM) is ~43% of the total concentration of cytidine triphosphates, yet the pool of CTP remains stable. This behavior suggests that the inhibition of viral replication by viperin is not the consequence of the limitation of the available pool of intracellular CTP, or other nucleotides, but rather is dependent on the generation of relevant concentrations of ddhCTP.

Figures 6A, 6B:
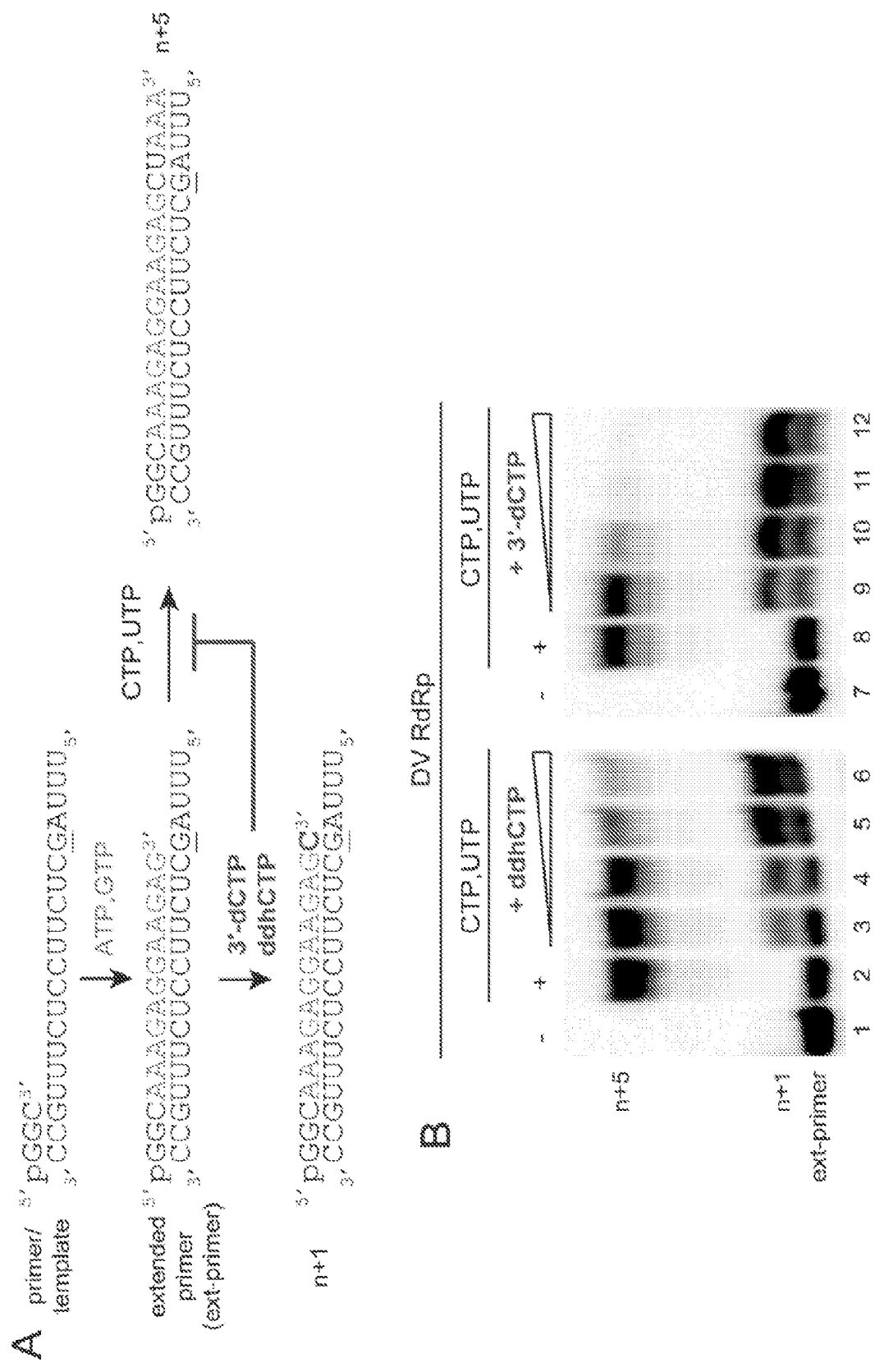
FIG. 6(A)-6(B): DV RdRp-catalyzed RNA synthesis is inhibited by ddhCTP by a chain termination mechanism. A. Schematic of primer extension assay for evaluating DV RdRp activity. Elongation complexes are first assembled with a trinucleotide primer, 5'-pGGC (SEQ ID NO:1), and 20-nt RNA template (SEQ ID NO:2) in the presence of ATP and GTP to elongate the trinucleotide primer (extended primer; SEQ ID NO:3)) and position the enzyme on the template (SEQ ID NO:2) such that guanosine is in the first templating position (underlined). In the presence of CTP and UTP, DV RdRp catalyzes RNA synthesis to the end of the template (SEQ ID NO:5). In the presence of ddhCTP or 3'-dCTP, these compounds have the ability to be incorporated, chain terminate RNA synthesis (SEQ ID NO:4) and prevent further extension by DV RdRp. B. Increasing concentrations of ddhCTP (1, 10, 100 and 300 μM) inhibits DV RdRp-catalyzed RNA synthesis. Reaction products resolved by denaturing PAGE from DV RdRp-catalyzed nucleoside incorporation in the presence of increasing concentrations of either ddhCTP or 3'-dCTP. In the absence of ddhCTP and 3'-dCTP, DV RdRp efficiently catalyzes RNA synthesis to the end of the template creating a 20-nt RNA product (n+5, lanes 2 and 8). However, with increasing concentrations of ddhCTP or 3'-dCTP, these compounds are utilized as substrates and once incorporated, they terminate RNA synthesis producing only a 16-nt product (n+1) (lanes 3-6 and 9-12).

Molecular target for ddhCTP: Viperin is induced by both DNA and RNA viruses (8,44-51). However, the presence of a 2'-OH on ddhCTP should almost certainly preclude efficient utilization by DNA polymerases, viral or cellular. (52) In contrast, 3'-deoxyribonucleotides are well known inhibitors of viral RNA-dependent RNA polymerases (RdRps) (53). Because Dengue virus (DV) and other members of the Flavivirus family are known to be sensitive to viperin, we used the DV RdRp as our model to examine the effect of ddhCTP on RdRp activity. First, it was asked if ddhCTP is a substrate for DV RdRp. To do so, a previously described primed-template assay was used. (54) A trinucleotide is used to prime RNA synthesis in the presence of two $^{32}$P-labeled rNTPs, producing a 15-nt product that is referred to here as the extended primer. Addition of CTP, 3'-dCTP or ddhCTP to the extended primer led to incorporation of all of these ribonucleotides. Addition of UTP to the CMP-incorporated RNA led to further extension to the end of template. However, addition of UTP to the 3'-dCMP- or ddhCMP-incorporated RNA did not support robust extension, as expected of a chain terminator. Some full-length product was observed in the presence of ddhCTP (>99% pure), which is due to contaminating CTP that could not be removed. A more stringent test of chain terminator effectiveness is whether it can directly compete with natural ribonucleotides. Therefore, RNA synthesis was evaluated in the presence of increasing concentrations of ddhCTP or 3'-dCTP (FIG. 6A). Both ddhCTP and 3'dCTP were incorporated and inhibited production of full-length RNA (FIG. 6B), with 3'-dCTP exhibiting greater efficacy than ddhCTP (compare lane 10 to lane 4 in FIG. 6B). The reduced efficacy of ddhCTP must be caused by the double bond between the 3' and 4' positions, and the corresponding impact on the detailed ribose conformation, as this is the only difference between ddhCTP and 3'-dCTP. The phylogeny of viral RdRp genes classifies these enzymes into three supergroups (55), with Flaviviral RdRps belonging to supergroup II. To determine if the observations with DV RdRp extend to other supergroups, we evaluated a member of supergroup I. Specifically, the RdRp from human rhinovirus type C (HRV-C) was used, a member of the Picornavirus family. Direct-incorporation experiments revealed utilization of both ddhCTP and 3'-dCTP by HRV-C RdRp. However, in the presence of other rNTPs, HRV-C RdRp was not inhibited by ddhCTP, even though it was inhibited by 3'-dCTP. It was concluded that not all RdRps are sensitive to ddhCTP, which suggests that different viruses will exhibit a range of susceptibilities to viperin expression in vivo.

Because members of the Flavivirus family are known to be sensitive to the catalytic activity of viperin, and the resemblance of ddhCTP to known polymerase chain terminators, the effect of ddhCTP on dengue virus (DV) RNA-dependent RNA polymerase (RdRp) activity was examined. First, it was demonstrated that ddhCTP is a substrate for DV RdRp using a primed-template assay. Addition of CTP, 3'-dCTP or ddhCTP led to incorporation of all of these nucleotides. Addition of UTP to the CMP-incorporated RNA, as expected, led to further extension to the end of template. However, addition of UTP to the 3'-dCMP- or ddhCMP-incorporated RNA did not support robust extension, as expected for the action of chain terminators.

A more stringent test of the effectiveness of a chain terminator is direct competition with natural ribonucleotides. Therefore, RNA synthesis was evaluated in the presence of increasing concentrations of ddhCTP or 3'-dCTP. Both ddhCTP and 3'dCTP were incorporated and inhibited production of full-length RNA. Additionally, by titrating ddhCTP at different concentrations of CTP the relative efficiency of utilization of ddhCTP was determined compared to CTP for DV RdRp, as well as the RdRp from West Nile Virus (WNV), another pathogenic flavivirus. This analysis yielded a 135- and 59-fold difference in utilization of ddhCTP relative to CTP for DV and WNV RdRps, respectively. Two additional members of the Flavivirus family, Zika virus (ZIKV) and HCV RdRps, were also evaluated. Both of these RdRps were susceptible to inhibition by ddhCTP utilization and chain termination, consistent with studies demonstrating the antiviral activity of viperin against these viruses.

These data show that the flavivirus RdRps would be susceptible to inhibition by ddhCTP during replication. Given the efficiency of utilization and genome size, it is calculated that even a ~1% probability of incorporating the ddhCTP chain terminator during replication would result in significant reduction of full-length genomes. To determine if the observations with the flavivirus RdRps extend to RdRps from other supergroups, members of supergroup I were evaluated. Specifically, the RdRps from human rhinovirus type C (HRV-C) and poliovirus (PV) were used, members of the Picornavirus family. Direct-incorporation experiments revealed utilization of both ddhCTP and 3'-dCTP by HRV-C RdRp. However, in the presence of other rNTPs, both HRV-C and PV RdRp were poorly inhibited by ddhCTP, even though both are inhibited by 3'-dCTP.

The above in vitro enzymatic characterizations suggest that ddhCTP is sufficient for the in vivo inhibition of viral replication. First, it was demonstrated that synthetic ddhC nucleoside was capable of traversing the plasma membrane of Vero and HEK293T cells and being metabolized to yield significant levels of ddhCTP (1 mM synthetic ddhC resulted in the intracellular accumulation of 129 µM and 78 µM ddh-CTP after 24 hr, respectively). Next, the historical African strain MR766 (Uganda 1947) and two contemporary strains PRVABC59 (Puerto Rico; 2015) and R103451 (Honduras; 2016, GenBank: KX262887) were used to evaluate the antiviral activity of ddhC towards ZIKV replication and release from Vero cells. Treatment with ddhC resulted in a 1-2 orders of magnitude reduction in ZIKV virus titers, which was dependent on dose, MOI, duration of infection and strain. For example, at an MOI of 0.1, 50-200-fold reduction in virus titer for ZIKV MR766 was observed at all time points, with reductions of 5-50-fold also being observed at MOI of 1.0. ZIKV R103451 (Honduras) and ZIKV PRVABC59 (Puerto Rico) exhibited analogous sensitivities to ddhC treatment. The reduction in viral release was not a result of ddhC cytotoxicity, as incubation with 1 mM ddhC did not alter Vero cell viability. These results, taken together with the above in vitro enzymatic analyses, are consistent with a model in which ddhC-derived ddhCTP inhibits viral replication through premature chain termination of RdRp products.

CONCLUSION

The antiviral benefits of IFN were first recognized in 1957 (56-61) Of the approximately 200 genes stimulated by IFN, most appear to function as negative effectors of antiviral activity, although most have not been fully characterized biochemically, nor have their precise roles in antiviral protection been defined. Herein, a new paradigm is disclosed for the antiviral function of viperin, which relies on its intrinsic catalytic activity to generate the previously undescribed replication chain inhibitor ddhCTP. To the inventors' knowledge, viperin is the only human protein that produces a small molecule capable of directly inhibiting viral replication machinery. Given the wide range of reported viperin-associated antiviral activities, ddhCTP will likely have significant clinical impact as a broad-spectrum antiviral.

REFERENCES (1) Molinari, N. A. M.; Ortega-Sanchez, I. R.; Messonnier, M. L.; Thompson, W. W.; Wortley, P. M.; Weintraub, E.; Bridges, C. B. *Vaccine* 2007, 25, 5086.
(2) Chin, K. C.; Cresswell, P. *P Natl Acad Sci USA* 2001, 98, 15125.
(3) Seo, J. Y.; Yaneva, R.; Cresswell, P. *Cell Host Microbe* 2011, 10, 534.
(4) Teng, T. S.; Foo, S. S.; Simamarta, D.; Lum, F. M.; Teo, T. H.; Lulla, A.; Yeo, N. K. W.; Koh, E. G. L.; Chow, A.; Leo, Y. S.; Merits, A.; Chin, K. C.; Ng, L. F. P. *J Clin Invest* 2012, 122, 4447.
(5) Szretter, K. J.; Brien, J. D.; Thackray, L. B.; Virgin, H. W.; Cresswell, P.; Diamond, M. S. *J Virol* 2011, 85, 11557.
(6) Upadhyay, A. S.; Vonderstein, K.; Pichlmair, A.; Stehling, O.; Bennett, K. L.; Dobler, G.; Guo, J. T.; Superti-Furga, G.; Lill, R.; Overby, A. K.; Weber, F. *Cell Microbiol* 2014, 16, 834.
(7) Wang, X. Y.; Hinson, E. R.; Cresswell, P. *Cell Host Microbe* 2007, 2, 96.
(8) Seo, J. Y.; Yaneva, R.; Hinson, E. R.; Cresswell, P. *Science* 2011, 332, 1093.
(9) Wang, S. S.; Wu, X. F.; Pan, T. T.; Song, W. H.; Wang, Y. H.; Zhang, F.; Yuan, Z. H. *J Gen Virol* 2012, 93, 83.
(10) Chan, Y. L.; Chang, T. H.; Liao, C. L.; Lin, Y. L. *J Virol* 2008, 82, 10455.
(11) Rivieccio, M. A.; Suh, H. S.; Zhao, Y. M.; Zhao, M. L.; Chin, K. C.; Lee, S. C.; Brosnan, C. F. *J Immunol* 2006, 177, 4735.
(12) Hee, J. S.; Cresswell, P. *Plos One* 2017, 12.
(13) Saitoh, T.; Satoh, T.; Yamamoto, N.; Uematsu, S.; Takeuchi, O.; Kawai, T.; Akira, S. *Immunity* 2011, 34, 352.
(14) Helbig, K. J.; Eyre, N. S.; Yip, E.; Narayana, S.; Li, K.; Fiches, G.; McCartney, E. M.; Jangra, R. K.; Lemon, S. M.; Beard, M. R. *Hepatology* 2011, 54, 1506.
(15) Helbig, K. J.; Carr, J. M.; Calvert, J. K.; Wati, S.; Clarke, J. N.; Eyre, N. S.; Narayana, S. K.; Fiches, G. N.; McCartney, E. M.; Beard, M. R. *Plos Neglect Trop D* 2013, 7.

(16) Akiva, E.; Brown, S.; Almonacid, D. E.; Barber, A. E.; Custer, A. F.; Hicks, M. A.; Huang, C. C.; Lauck, F.; Mashiyama, S. T.; Meng, E. C.; Mischel, D.; Morris, J. H.; Ojha, S.; Schnoes, A. M.; Stryke, D.; Yunes, J. M.; Ferrin, T. E.; Holliday, G. L.; Babbitt, P. C. *Nucleic Acids Res* 2014, 42, D521.

(17) Booker, S. J. *Curr Opin Chem Biol* 2009, 13, 58.

(18) Challand, M. R.; Driesener, R. C.; Roach, P. L. *Nat Prod Rep* 2011, 28, 1696.

(19) Sofia, H. J.; Chen, G.; Hetzler, B. G.; Reyes-Spindola, J. F.; Miller, N. E. *Nucleic Acids Res* 2001, 29, 1097.

(20) Dey, A.; Peng, Y.; Broderick, W. E.; Hedman, B.; Hodgson, K. O.; Broderick, J. B.; Solomon, E. I. *J Am Chem Soc* 2011, 133, 18656.

(21) Walsby, C. J.; Ortillo, D.; Yang, J.; Nnyepi, M. R.; Broderick, W. E.; Hoffman, B. M.; Broderick, J. B. *Inorg Chem* 2005, 44, 727.

(22) Seo, J. Y.; Cresswell, P. *Plos Pathog* 2013, 9.

(23) Shaveta, G.; Shi, J. H.; Chow, V. T. K.; Song, J. X. *Biochem Bioph Res Co* 2010, 391, 1390.

(24) Hinson, E. R.; Cresswell, P. *J Biol Chem* 2009, 284, 4705.

(25) Duschene, K. S.; Broderick, J. B. *Biomolecular concepts* 2012, 3, 255.

(26) Duschene, K. S.; Broderick, J. B. *FEBS letters* 2010, 584, 1263.

(27) Makins, C.; Ghosh, S.; Roman-Melendez, G. D.; Malec, P. A.; Kennedy, R. T.; Marsh, E. N. *J Biol Chem* 2016, 291, 26806.

(28) Marcotte, E. M.; Pellegrini, M.; Ng, H. L.; Rice, D. W.; Yeates, T. O.; Eisenberg, D. *Science* 1999, 285, 751.

(29) Lei, M. M.; Liu, H. H.; Liu, S. S.; Zhang, Y.; Zhang, S. C. *Dev Comp Immunol* 2015, 53, 293.

(30) Petrova, M.; Budesinsky, M.; Rosenberg, I. *Tetrahedron Lett* 2010, 51, 6874.

(31) Hanzelmann, P.; Schindelin, H. *P Natl Acad Sci USA* 2004, 101, 12870.

(32) Silakov, A.; Grove, T. L.; Radle, M. I.; Bauerle, M. R.; Green, M. T.; Rosenzweig, A. C.; Boal, A. K.; Booker, S. J. *J Am Chem Soc* 2014, 136, 8221.

(33) Kennedy, A. D.; Porcella, S. F.; Martens, C.; Whitney, A. R.; Braughton, K. R.; Chen, L.; Craig, C. T.; Tenover, F. C.; Kreiswirth, B. N.; Musser, J. M.; DeLeo, F. R. *Journal of clinical microbiology* 2010, 48, 4504.

(34) Ferraro, P.; Franzolin, E.; Pontarin, G.; Reichard, P.; Bianchi, V. *Nucleic Acids Res* 2010, 38.

(35) Minnihan, E. C.; Nocera, D. G.; Stubbe, J. *Accounts Chem Res* 2013, 46, 2524.

(36) Schwarz, H. A.; Dodson, R. W. *J Phys Chem-Us* 1989, 93, 409.

(37) Grove, T. L.; Radle, M. I.; Krebs, C.; Booker, S. J. *J Am Chem Soc* 2011, 133, 19586.

(38) Grove, T. L.; Livada, J.; Schwalm, E. L.; Green, M. T.; Booker, S. J.; Silakov, A. *Nat Chem Biol* 2013, 9, 422.

(39) Kambara, H.; Niazi, F.; Kostadinova, L.; Moonka, D. K.; Siegel, C. T.; Post, A. B.; Carnero, E.; Barriocanal, M.; Fortes, P.; Anthony, D. D.; Valadkhan, S. *Nucleic Acids Res* 2014, 42, 10668.

(40) Xu, Y. J.; Johansson, M.; Karlsson, A. *J Biol Chem* 2008, 283, 1563.

(41) Wang, B.; Fang, Y.; Wu, Y.; Koga, K.; Osuga, Y.; Lv, S.; Chen, D.; Zhu, Y.; Wang, J.; Huang, H. *Placenta* 2015, 36, 667.

(42) Severa, M.; Coccia, E. M.; Fitzgerald, K. A. *J Biol Chem* 2006, 281, 26188.

(43) Tang, H. B.; Lu, Z. L.; Wei, X. K.; Zhong, T. Z.; Zhong, Y. Z.; Ouyang, L. X.; Luo, Y.; Xing, X. W.; Liao, F.; Peng, K. K.; Deng, C. Q.; Minamoto, N.; Luo, T. R. *Sci Rep-Uk* 2016, 6.

(44) Chin, K. C.; Cresswell, P. *Proceedings of the National Academy of Sciences of the United States of America* 2001, 98, 15125.

(45) Helbig, K. J.; Carr, J. M.; Calvert, J. K.; Wati, S.; Clarke, J. N.; Eyre, N. S.; Narayana, S. K.; Fiches, G. N.; McCartney, E. M.; Beard, M. R. *PLoS neglected tropical diseases* 2013, 7, e2178.

(46) Proud, D.; Turner, R. B.; Winther, B.; Wiehler, S.; Tiesman, J. P.; Reichling, T. D.; Juhlin, K. D.; Fulmer, A. W.; Ho, B. Y.; Walanski, A. A.; Poore, C. L.; Mizoguchi, H.; Jump, L.; Moore, M. L.; Zukowski, C. K.; Clymer, J. W. *American journal of respiratory and critical care medicine* 2008, 178, 962.

(47) Seo, J. Y.; Yaneva, R.; Cresswell, P. *Cell host & microbe* 2011, 10, 534.

(48) Szretter, K. J.; Brien, J. D.; Thackray, L. B.; Virgin, H. W.; Cresswell, P.; Diamond, M. S. *Journal of virology* 2011, 85, 11557.

(49) Teng, T. S.; Foo, S. S.; Simamarta, D.; Lum, F. M.; Teo, T. H.; Lulla, A.; Yeo, N. K.; Koh, E. G.; Chow, A.; Leo, Y. S.; Merits, A.; Chin, K. C.; Ng, L. F. *J Clin Invest* 2012, 122, 4447.

(50) Upadhyay, A. S.; Vonderstein, K.; Pichlmair, A.; Stehling, O.; Bennett, K. L.; Dobler, G.; Guo, J. T.; Superti-Furga, G.; Lill, R.; Overby, A. K.; Weber, F. *Cellular microbiology* 2014, 16, 834.

(51) Zhang, Y.; Burke, C. W.; Ryman, K. D.; Klimstra, W. B. *J Virol* 2007, 81, 11246.

(52) Brown, J. A.; Suo, Z. *Biochemistry* 2011, 50, 1135.

(53) Shim, J.; Larson, G.; Lai, V.; Naim, S.; Wu, J. Z. *Antiviral research* 2003, 58, 243.

(54) Van Slyke, G. A.; Arnold, J. J.; Lugo, A. J.; Griesemer, S. B.; Moustafa, I. M.; Kramer, L. D.; Cameron, C. E.; Ciota, A. T. *Plos Pathog* 2015, 11, e1005009.

(55) Koonin, E. V. *J Gen Virol* 1991, 72 (Pt 9), 2197.

(56) Isaacs, A.; Lindenmann, J. *Proceedings of the Royal Society of London. Series B, Biological sciences* 1957, 147, 258.

(57) Zhang, Y.; Chen, B.; Wang, L.; Chi, J.; Song, S.; Liu, M.; Zhao, Z. *Revista espanola de enfermedades digestivas: organo oficial de la Sociedad Espanola de Patologia Digestiva* 2016, 108, 263.

(58) Scrivo, R.; Sauzullo, I.; Mengoni, F.; Riccieri, V.; Altieri, A. M.; Cantoro, L.; Vullo, V.; Mastroianni, C. M.; Valesini, G. *Clinical rheumatology* 2016, 35, 1383.

(59) Machado, M. O.; Oriolo, G.; Bortolato, B.; Kohler, C. A.; Maes, M.; Solmi, M.; Grande, I.; Martin-Santos, R.; Vieta, E.; Carvalho, A. F. *Journal of affective disorders* 2017, 209, 235.

(60) Gaetani, L.; Menduno, P. S.; Cometa, F.; Di Gregorio, M.; Sarchielli, P.; Cagini, C.; Calabresi, P.; Di Filippo, M. *Journal of neurology* 2016, 263, 422.

(61) Aminizadeh, E.; Alavian, S. M.; Akbari Sari, A.; Ebrahimi Daryani, N.; Behnava, B. *Hepatitis monthly* 2016, 16, e28537.

What is claimed is:

1. A compound or pharmaceutical salt thereof, wherein the compound is selected from the group consisting of Formula I, Formula II, Formula III, Formula IV, Formula V, Formula VI, Formula VII, Formula VIII, and Formula IX;

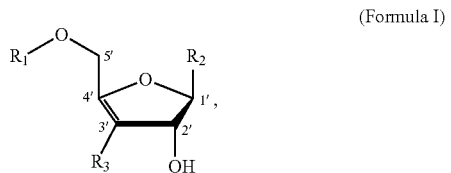
(Formula I)

wherein, in Formula I, $R_1$ is a hydrogen, alkyl, benzyl, aryl, acycloxyalkyl, alkoxycarbonyloxy alkyl, or S-acylthioalkyl; and $R_2$ is an adenine, guanosine, cytosine, uridine, or thymidine; and $R_3$ is a hydrogen, hydroxyl, thiol, halide, or alkyl, provided that when $R_1$ is a hydrogen and $R_2$ is cytosine, guanosine, uridine, thymidine or adenine, $R_3$ is not hydrogen;

and

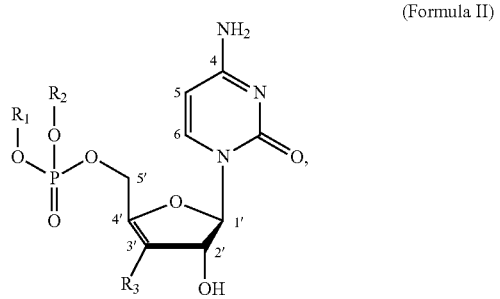
(Formula II)

wherein, in Formula II, $R_1$ and $R_2$ are each, independently, a hydrogen, alkyl, benzyl, aryl, acycloxyalkyl, alkoxycarbonyloxy alkyl, or S-acylthioalkyl; and $R_3$ is a hydrogen, hydroxyl, thiol, halide, or alkyl, and

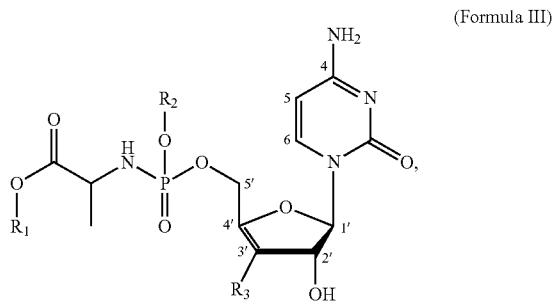
(Formula III)

wherein, in Formula III, $R_1$ and $R_2$ are each, independently, a hydrogen, alkyl, benzyl, aryl, acycloxyalkyl, alkoxycarbonyloxy alkyl, or S-acylthioalkyl; and $R_3$ is hydrogen, hydroxyl, thiol, halide, or alkyl, and

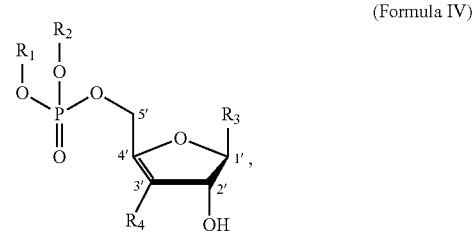
(Formula IV)

wherein, in Formula IV, $R_1$ and $R_2$ are each, independently, a hydrogen, alkyl, benzyl, aryl, acycloxyalkyl, alkoxycarbonyloxy alkyl, or S-acylthioalkyl;

$R_3$ is adenine, guanosine, cytosine, uridine, or thymidine; and $R_4$ is hydrogen, hydroxyl, thiol, halide, or alkyl, and

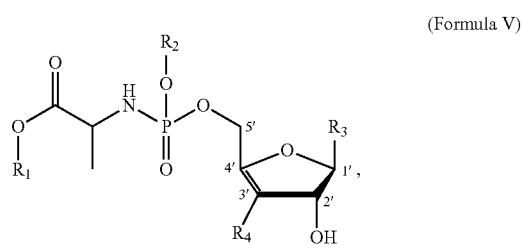
(Formula V)

wherein, in Formula V, $R_1$ and $R_2$ are each, independently, a hydrogen, alkyl, benzyl, aryl, acycloxyalkyl, alkoxycarbonyloxy alkyl, or S-acylthioalkyl;

$R_3$ is adenine, guanosine, cytosine, uridine, or thymidine; and $R_4$ is hydrogen, hydroxyl, thiol, halide, or alkyl, and

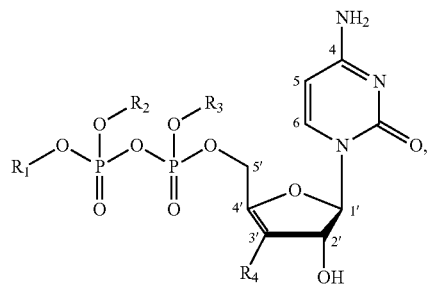
(Formula VI)

wherein, in Formula VI, $R_1$, $R_2$, and $R_3$ are each, independently, a hydrogen, alkyl, benzyl, aryl, acycloxyalkyl, alkoxycarbonyloxy alkyl, or S-acylthioalkyl; and $R_4$ is hydrogen, hydroxyl, thiol, halide, or alkyl, and

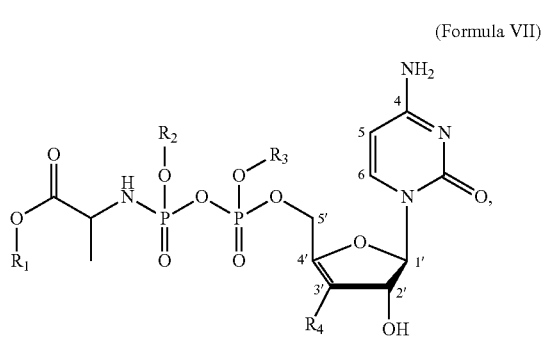
(Formula VII)

wherein, in Formula VII, $R_1$, $R_2$, and $R_3$ are each, independently, a hydrogen, alkyl, benzyl, aryl, acycloxyalkyl, alkoxycarbonyloxy alkyl, or S-acylthioalkyl; and $R_4$=hydrogen, hydroxyl, thiol, halide, or alkyl, and

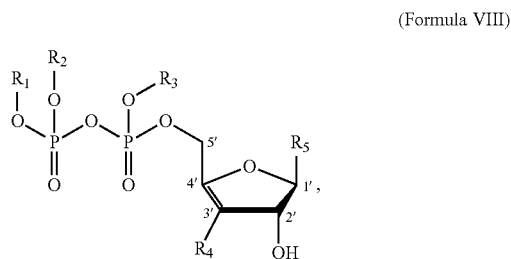
(Formula VIII)

wherein, in Formula VIII, $R_1$, $R_2$, and $R_3$ are each, independently, a hydrogen, alkyl, benzyl, aryl, acycloxyalkyl, alkoxycarbonyloxy alkyl, or S-acylthioalkyl;

$R_5$ is adenine, guanosine, cytosine, uridine, or thymidine; and $R_4$ is hydrogen, hydroxyl, thiol, halide, or alkyl, and

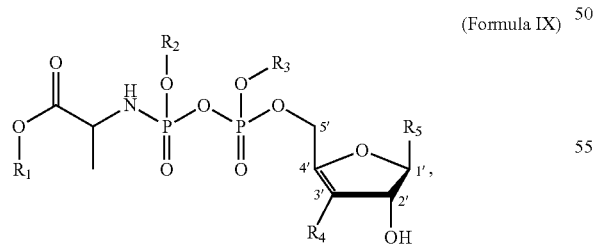
(Formula IX)

wherein, in Formula IX, $R_1$, $R_2$, and $R_3$ are each, independently, a hydrogen, alkyl, benzyl, aryl, acycloxyalkyl, alkoxycarbonyloxy alkyl, or S-acylthioalkyl;

$R_5$ is adenine, guanosine, cytosine, uridine, or thymidine; and $R_4$ is hydrogen, hydroxyl, thiol, halide, or alkyl.

2. A non-naturally occurring compound or pharmaceutical salt thereof, wherein the compound has the following formula:

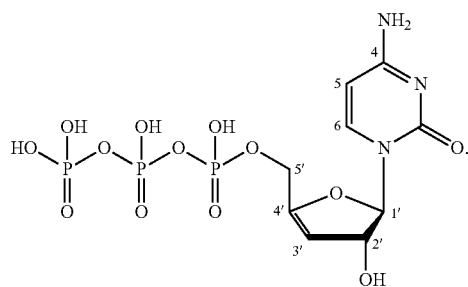 [SMILES: Nc1ccn([C@@H]2OC(COP(=O)(O)OP(=O)(O)OP(=O)(O)O)=C[C@@H]2O)c(=O)n1]

3. The compound or pharmaceutical salt thereof of claim 1, wherein the compound is represented by Formula II.
4. The compound or pharmaceutical salt thereof of claim 1, wherein the compound is represented by Formula III.
5. The compound or pharmaceutical salt thereof of claim 1, wherein the compound is represented by Formula VI.
6. The compound or pharmaceutical salt thereof of claim 1, wherein the compound is represented by Formula VII.
7. A pharmaceutical composition comprising the compound or pharmaceutical salt thereof of claim 1.
8. The pharmaceutical composition of claim 7, comprising a pharmaceutically acceptable carrier.
9. A pharmaceutical composition comprising the compound or pharmaceutical salt thereof of claim 2.
10. A method of treating a flavivirus infection in a subject comprising administering to the subject an effective amount of the compound or pharmaceutical salt thereof of claim 1, or a compound of Formula I' or a pharmaceutical salt thereof,

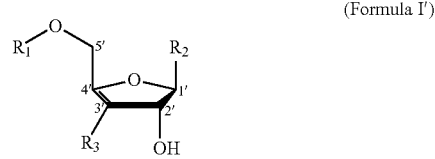
(Formula I')

wherein $R_1$ is a hydrogen and $R_2$ is cytosine, guanosine, uridine, thymidine or adenine, and $R_3$ is hydrogen; or

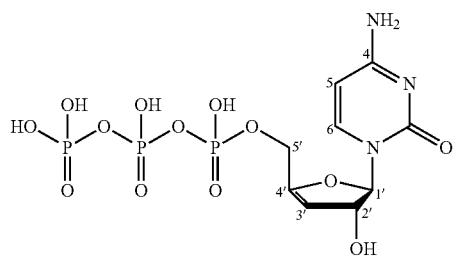 [SMILES: Nc1ccn([C@@H]2OC(COP(=O)(O)OP(=O)(O)OP(=O)(O)O)=C[C@@H]2O)c(=O)n1]

in an effective amount to treat a flavivirus infection.

11. The method of claim 10, wherein the flavivirus infection is a Dengue virus infection, Zika virus infection, or West Nile virus infection.

12. A method of treating a viral infection in a subject comprising administering to the subject an effective amount of the compound or pharmaceutical salt thereof of claim 1, or a compound of Formula I' or a pharmaceutical salt thereof,

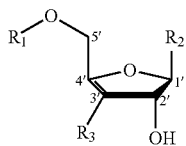

(Formula I')

wherein $R_1$ is a hydrogen and $R_2$ is cytosine, guanosine, uridine, thymidine or adenine, and $R_3$ is hydrogen;

or

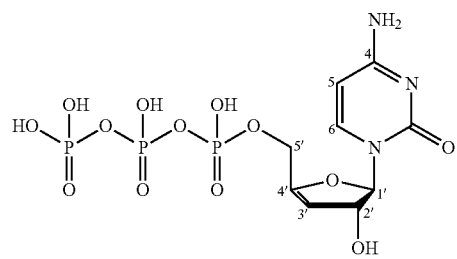

in an effective amount to treat a viral infection.

13. The method of claim 12, wherein the viral infection is an influenza virus infection or a hepatitis C virus infection or an HIV infection.

14. A method of inhibiting a viral RNA-dependent RNA-polymerase comprising contacting the viral RNA-dependent RNA-polymerase in a cell with an effective amount of the compound or pharmaceutical salt thereof of claim 1, or a compound of Formula I' or a pharmaceutical salt thereof,

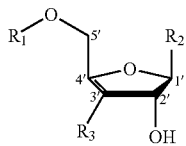

(Formula I')

wherein $R_1$ is a hydrogen and $R_2$ is cytosine, guanosine, uridine, thymidine or adenine, and $R_3$ is hydrogen;

or

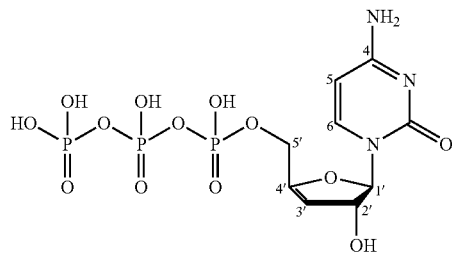 [SMILES: Nc1ccn([C@@H]2OC(COP(=O)(O)OP(=O)(O)OP(=O)(O)O)=C[C@@H]2O)c(=O)n1]

in an effective amount to inhibit a viral RNA-dependent RNA-polymerase.

15. A method of inhibiting multiplication of a virus, which virus uses or expresses a viral RNA-dependent RNA-polymerase, comprising contacting the virus with an effective amount of the compound or pharmaceutical salt thereof of claim 1, or a compound of Formula I' or a pharmaceutical salt thereof,

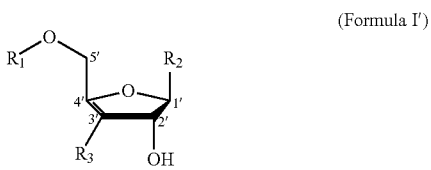

(Formula I')

wherein $R_1$ is a hydrogen and $R_2$ is cytosine, guanosine, uridine, thymidine or adenine, and $R_3$ is hydrogen;

or

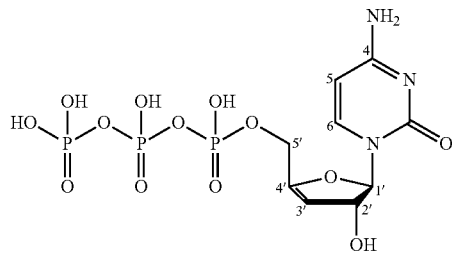 [SMILES: Nc1ccn([C@@H]2OC(COP(=O)(O)OP(=O)(O)OP(=O)(O)O)=C[C@@H]2O)c(=O)n1]

in an effective amount to inhibit viral multiplication.

16. The method of claim 15, wherein the compound is represented by Formula II.

17. The method of claim 15, wherein the compound is represented by Formula III.

18. The method of claim 15, wherein the compound is represented by Formula VI.

19. The method of claim 15, wherein the compound is represented by Formula VII.

* * * * *